United States Patent [19]

Banks et al.

[11] 4,258,204

[45] Mar. 24, 1981

[54] ACRYLATE ESTER MONOMER PRODUCTION

[75] Inventors: Allen R. Banks, Lakewood; Richard F. Fibiger, Boulder; Ted Jones, Lakewood, all of Colo.

[73] Assignee: University Patents, Inc., Norwalk, Conn.

[21] Appl. No.: 963,272

[22] Filed: Nov. 24, 1978

[51] Int. Cl.³ .............................................. C07C 69/52
[52] U.S. Cl. .................................................... 560/205
[58] Field of Search ........................................ 560/205

[56] References Cited

U.S. PATENT DOCUMENTS 3,106,593  10/1963  Benesi et al. ................. 260/681.5 R

OTHER PUBLICATIONS

Kirk—Othmer, "Encyclopedia of Chemical Technology", 2nd Ed. vol. 13, p. 344.

Ibid. vol. 8, pp. 337-338.
Krasnyl, E. B. et al., "Adsorption of Hydrogen Chlorides on Synthetic Zeolites.", Zh. Prikl. Khim. 1970, 43(11), 2449-2453, (See Chemical Abstracts, vol. 74, 1971, #68,083n.)
Chemical Abstracts, 9th Coll Index. p. 27, 228CS.

Primary Examiner—Natalie Trousof
Assistant Examiner—L. Hendriksen
Attorney, Agent, or Firm—Donald W. Margolis; H. Kenneth Johnston, II; A. Sidney Alpert

[57] ABSTRACT

Acrylate ester monomers are produced in high yield and without polymerization by reacting an $\alpha,\beta$-unsaturated organic acid halide and a hydroxyl containing organic compound in the presence of molecular sieves. In the absence of molecular sieves the same reactants produce the monomer ester products in low yield and/or form polymers.

9 Claims, No Drawings

ACRYLATE ESTER MONOMER PRODUCTION

BACKGROUND OF THE INVENTION

1. Field of the Invention

The present invention relates to methods of producing monomeric acrylate esters. More specifically it relates to methods of producing acrylate esters by reacting an $\alpha,\beta$-unsaturated acrylic organic acid halide and a hydroxyl containing organic compound in the presence of molecular sieves. In some instances novel acrylate ester monomers are produced.

2. Prior Art

Liquid processes for the syntheses of monomeric acrylate esters have normally required many steps and have produced the desired reaction products in only limited yields. In one prior art reaction system when methacryloyl chloride and an alcohol have been reacted in the presence of triethylamine, monomeric methacrylate esters are produced in only about 30% to about 45% isolated yield. In another prior art reaction system, transesterification of methyl methacrylate with alcohol and an acid catalyst, has also resulted in a low monomeric ester yield. In these typical prior art reactions it is believed that traces of free hydrogen halide acid in the reaction system has favored the competing polymerization reaction of the reactive $\alpha,\beta$-unsaturated esters. This has resulted in the production of unwanted polymers which causes low yield of the desired ester monomer. Either the unreacted starting materials or other products produced during such prior art reactions often exhibit boiling points closely approximating those of the desired monomer, and are thus difficult to separate from the ester monomer by distillation. Furthermore, once acrylate monomers are produced by prior art techniques they remain susceptible to polymerization, and thus further reduce the isolable yield of ester during both purification and storage.

Molecular sieves have been utilized as drying agents for organic solvents, to trap water generated during reactions and to scavenge small molecules. They have not been known to be previously utilized in the production of monomeric acrylate esters.

BRIEF DESCRIPTION OF THE INVENTION

The present invention produces acrylate ester monomers by reacting an $\alpha,\beta$-unsaturated organic acid halide and a hydroxyl containing organic compound in the presence of molecular sieves. Molecular sieves, of about 2 Å to about 4 Å have been found to be useful in the practice of the present invention, with 3 Å molecular sieves being preferred. Molecular sieves in the necessary size range are commercially available from many sources and normally are provided in the form of aluminosilicates, such as zeolites.

The method of the present invention has been found to be effective with hydroxyl containing organic compounds including primary alcohols, secondary alcohols, tertiary alcohols, benzylic alcohols and phenols to form monomeric acrylate esters in good to excellent yields.

The general reaction is as follows:

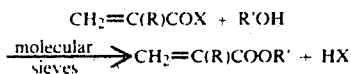

wherein

R is —H or —CH$_3$,
R' is an alkyl or aryl radical, and
X is a halogen ion.

Many solvents have been found to be useful during these reactions, with inexpensive and readily available carbon tetrachloride, ethylene chloride or acetonitrile being preferred, the latter being especially useful for compounds which are not soluble in carbon tetrachloride. A wide range of additional organic solvents may be utilized in the process, so long as the reactants are soluble therein; however, oxygen-containing solvents have been found to provide less favorable results.

As an additional benefit of the process of the present invention, the presence of molecular sieves appears to prevent polymerization of the reactants as well as the reaction products. This allows storage of reactants for extended periods and extended reaction times without the formation of undesirable by-products or polymers.

Separation and isolation of the monomeric ester products produced by the reactions of the present invention is achieved by the simple expedient of filtering the molecular sieves from the cooled reaction mixture. This is followed by evaporation of the solvent, preferably under reduced pressure. This evaporation step also provides for the removal of any volatile unreacted starting materials. Where additional purification of the ester monomer is desired it can be obtained, for example, by simple vacuum distillation. In instances in which temperatures in excess of 100° C. are required for distillation, purification is accomplished by either short-path distillation or by recrystalization.

The monomeric acrylate ester reaction products of the present invention have been found to retain their chemical integrity and avoid the formation of polymers by storing them at low temperatures in the presence of molecular sieves. Such procedures minimize polymerization during prolonged storage while allowing immediate access to the pure monomeric compounds by the simple expedient of filtering or decanting the product.

While the exact benefit provided by the utilization of molecular sieves in the reactions of the present invention is not known, it is theorized that the sieves trap or scavenge the hydrogen halide acid by-product, thus cancelling its availability to initiate competing polymerization reactions.

Following the various procedures detailed herein the acrylate ester monomers of the present invention can be easily produced by persons having skill in the art. However, the descriptions, specific examples and representative reactants and solvents detailed and described herein are set forth as preferred embodiments and are not intended to limit the scope of the invention.

DETAILED DESCRIPTION OF THE INVENTION

The practice of the present invention may take many forms. In the most common embodiment an $\alpha,\beta$-unsaturated organic halide is reacted with a hydroxyl containing compound in the presence of molecular sieves. In preferred embodiments methacryloyl chloride is reacted in a single step with an alcohol in the presence of molecular sieves in the range of about 2 Å to about 4 Å. This preferred process produces methacrylate ester monomers in high yield. The general procedure is as follows:

General Procedure

To 4 g of powdered 3 Å molecular sieves, obtained from Davison Chemical Company and dried under vacuum, is added 20 mmol of the selected hydroxyl containing compound dissolved in 40 ml of solvent, such as carbon tetrachloride. To this mixture is added a stoichiometric amount of α,β-unsaturated organic acid halide. This reaction mixture is then refluxed until the reaction is completed. Subsequently, the reaction mixture is cooled to room temperature and the molecular sieves removed by filtration. Then solvent and unreacted volatile starting materials are removed by evaporation under reduced pressure to yield the crude monomeric product. High yield pure ester products are obtained by either recrystallization of solids or distillation of liquids under reduced pressure.

The following table sets forth several non-limiting preferred embodiments of the present invention.

and the vacuum adapter is removed. Solvent in the form of 50 ml of carbon tetrachloride is then added to the flask along with 25 mmol of 3-methyl-3-pentanol and 25 mmol of methacryloyl chloride. A magnetic stirring bar is added to the contents of the flask and a condenser with a drying tube is attached to the neck of the flask. Then the flask and its contents are placed in a hot water bath and heated for 185 hours while being subjected to magnetic stirring. The contents of the flask are then cooled and filtered through a celite pad, filtered through a 20 cm $Al_2O_3$ column, the column washed with 100 ml of $CH_2Cl_2$ and the solvents are then evaporated under reduced pressure. The resulting product is pure monomeric 3-methyl-3-pentyl methacrylate ester.

The completion of the various reactions of the present invention are monitored by determining the absence of starting material in the mixture, for example, by using NMR or thin layer chromatography techniques.

The various methacrylate ester monomers produced

PRODUCTION OF ACRYLATE ESTER MONOMERS

| | α,β-unsaturated organic acid halide | Hydroxyl Compound | Reaction Product | Isolated Yield % | Reaction Time, Hours |
|---|---|---|---|---|---|
| 1. | $CH_2=C(CH_3)CCl$ Methacryloyl Chloride | $CH_3(CH_2)_3OH$ n-butanol | $CH_3(CH_2)_3-OC(CH_3)C=CH_2$ (O) n-butyl methacrylate | 91 | 13 |
| 2. | $CH_2=C(CH_3)CCl$ Methacryloyl Chloride | $C_5H_4OH$ cyclopentanol | $C_5H_4-OC(CH_3)C=CH_2$ (O) cyclopentyl methacrylate | 95 | 20 |
| 3. | $CH_2=C(CH_3)CCl$ Methacryloyl Chloride | $(CH_3CH_2)_2CH_3COH$ 3-methyl-3-pentanol | $(CH_3CH_2)_2CH_3C-OC(CH_3)C=CH_2$ (O) 3-methyl-3-pentyl methacrylate | 50(100)$^a$ | 185 |
| 4. | $CH_2=C(CH_3)CCl$ Methacryloyl Chloride | $C_6H_5CH_2OH$ benzyl alcohol | $C_6H_5CH_2-OC(CH_3)C=CH_2$ (O) benzyl methacrylate | 85 | 12 |
| 5. | $CH_2=C(CH_3)CCl$ Methacryloyl Chloride | $C_6H_5OH$ phenol | $C_6H_5-OC(CH_3)C=CH_2$ (O) phenyl methacrylate | 98 | 39 |
| 6. | $CH_2=C(CH_3)CCl$ Methacryloyl Chloride | $m\text{-}CH_3C_6H_4OH$ m-methyl phenol | $m\text{-}CH_3C_6H_4-OC(CH_3)C=CH_2$ (O) m-methyl phenyl methacrylate | 93 | 50 |
| 7. | $CH_2=C(CH_3)CCl$ Methacryloyl Chloride | $p\text{-}NO_2C_6H_4OH$ p-nitro phenol | $p\text{-}NO_2C_6H_4-OC(CH_3)C=CH_2$ (O) p-nitro phenyl methacrylate | 74 | 56 |
| 8. | $CH_2=C(CH_3)CCl$ Methacryloyl Chloride | $p\text{-}ClC_6H_4OH$ p-chloro phenyl | $p\text{-}ClC_6H_4-OC(CH_3)C=CH_2$ (O) p-chloro phenyl methacrylate | 94 | 56 |
| 9. | $CH_2=C(CH_3)CCl$ Methacryloyl Chloride | $m\text{-}ClC_6H_4OH$ m-chloro phenol | $m\text{-}ClC_6H_4-OC(CH_3)C=CH_2$ (O) m-chloro phenyl methacrylate | 87 | 60 |
| 10. | $CH_2=C(CH_3)CCl$ Methacryloyl Chloride | $o\text{-}ClC_6H_4OH$ o-chloro-phenol | $o\text{-}ClC_6H_4-OC(CH_3)C=CH_2$ (O) o-chloro phenyl methacrylate | 93 | 160 |

$^a$yield based on reacted alcohol

The following detailed example is set forth to further clarify the process of the present invention.

Production of 3-Methyl-3-Pentyl Methacrylate

Into a 100 ml long neck round bottom flask with a vacuum adapter is placed about 2 g of 3 Å molecular sieves. The flask is connected to a vacuum line and placed under reduced pressure of about 0.02 mm of Hg. It is then heated, causing gas (air) to evolve from the sieves. Heating is continued until gas evolution ceases. Then the flask is allowed to cool to room temperature by the present invention have utility as adhesives, antitumor agents, or as starting products for various polymers.

The practice of the present invention allows simple and high yield production of acrylate ester monomers in liquid systems. Several of the resulting monomers are novel. Only a single simple step is required to complete the reaction. While the reaction times themselves may be quite long, such extended reaction times allow for high yields. The presence of the molecular sieves appears to allow the reactions to proceed without any interferring or competing polymerization reactions which limit the yield.

It will be understood that the reactions shown are merely illustrative and are not to be taken as limitations of the invention, it being understood that, in general, the process of the present invention may be utilized in connection with any esterification of any equivalent acid halide with a suitable hydroxyl containing organic compound. The reaction system parameters are generally not a limiting factor, although it is desirable to utilize stochiometric proportions of the reactants in order to avoid wasting any of the starting materials.

While the invention has been particularly described and shown with reference to preferred examples disclosing the use of molecular sieves during the reaction of methacryloyl chloride and various hydroxyl containing compounds, it will be understood by those skilled in the art that other $\alpha,\beta$-unsaturated acid halides, molecular sieves and other hydroxyl containing starting materials may be utilized in the practice of the present invention without departing from the spirit and the scope thereof.

What is claimed is:

1. In a process for producing acrylate ester monomers by mixing and reacting the corresponding $\alpha,\beta$-unsaturated organic acid halide and a hydroxyl containing organic compound in an organic solvent for the reactants, the improvement which consists of carrying out the reaction in the presence of molecular sieves in the range of about 2 A° to about 4 A° and in an amount sufficient to substantially avoid the production of polymers, whereby substantially pure $\alpha,\beta$-unsaturated ester monomers are produced in yields of 50% or greater, based on the starting materials, and without any substantial polymer production.

2. The process of claim 1 wherein the hydroxyl containing organic compound is selected from the group consisting of primary alcohols, secondary alcohols, tertiary alcohols, benzylic alcohols and phenols.

3. The process of claim 1 wherein the $\alpha,\beta$-unsaturated organic acid halide is an acrylic compound.

4. The process of claim 3 wherein the $\alpha,\beta$-unsaturated acrylic organic acid halide is methacryloyl chloride.

5. The process of claim 1 wherein the $\alpha,\beta$-unsaturated acid halide is methacryloyl chloride and the hydroxyl containing organic compound is selected from the group consisting of primary alcohols, secondary alcohols, tertiary alcohols, benzylic alcohols and phenols.

6. The process of claim 1 wherein the molecular sieves are about 3 A.

7. The process of claim 1 wherein the $\alpha,\beta$-unsaturated acid halide is methacryloyl chloride, the hydroxyl containing organic compound is selected from the group consisting of n-butanol, cyclo-pentanol, 3-methyl-3-pentanol, benzyl alcohol, phenol, m-methyl phenol, p-nitro phenol, p-chloro-phenol, m-chloro-phenol and o-chloro-phenol.

8. The process of claim 7 wherein the hydroxyl containing organic compound is 3-methyl-3-pentanol.

9. The process of claim 1, wherein the organic solvent is selected from the group consisting of carbon tetrachloride, ethylene chloride, and acetonitrile.

* * * * *